United States Patent [19]

Jacquet et al.

[11] 4,395,541
[45] Jul. 26, 1983

[54] IONENE POLYMER AND PREPARATION THEREOF

[75] Inventors: Bernard Jacquet, Antony; Gérard Lang, Epinay sur Seine; Alain Malaval, Aulnay sous Bois; Serge Forestier, Claye Souilly; Do Le Trung, Drancy, all of France

[73] Assignee: Societe Anonyme dite: L'Oreal, Paris, France

[21] Appl. No.: 217,402

[22] Filed: Dec. 17, 1980

[30] Foreign Application Priority Data

Dec. 21, 1979 [FR] France .................. 79 31430

[51] Int. Cl.$^3$ ............................................. C08G 73/00
[52] U.S. Cl. .................................. 528/367; 525/535; 525/540; 528/220; 528/229; 528/259; 528/261; 528/265; 528/335; 528/336; 528/363; 528/391; 528/392; 528/397; 528/422; 528/423; 424/70
[58] Field of Search ............... 528/367, 335, 336, 229, 528/220, 397, 422, 423, 392, 363, 259, 265, 261, 391; 525/535, 540

[56] References Cited

U.S. PATENT DOCUMENTS

| | | | |
|---|---|---|---|
| 3,671,468 | 6/1972 | Tsuda et al. | 528/335 |
| 3,856,714 | 12/1974 | Moore et al. | 528/336 |
| 4,075,136 | 2/1978 | Schaper | 528/422 |
| 4,157,388 | 6/1979 | Christiansen | 528/390 |
| 4,166,894 | 9/1979 | Schaper | 528/321 |
| 4,254,255 | 3/1981 | Lobach et al. | 528/312 |

OTHER PUBLICATIONS

U.S.P. 3,306,875, cols. 1-2, 35-36.

Primary Examiner—Harold D. Anderson
Attorney, Agent, or Firm—Cushman, Darby & Cushman

[57] ABSTRACT

Ionene polymers have been prepared and have been found to be useful in cosmetic compositions for the treatment of the hair and skin, or in the treatment of natural or synthetic textile fibers. These polymers comprise units of the formula

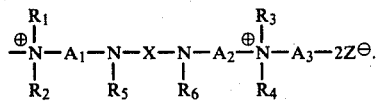

19 Claims, No Drawings

IONENE POLYMER AND PREPARATION THEREOF

The present invention relates to new ionene type polymers, to their preparation and to their use.

More specifically, the present invention relates to polymers having units of the formula:

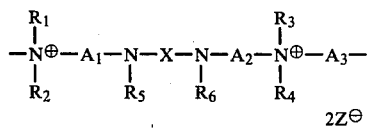

wherein $R_1$, $R_2$, $R_3$ and $R_4$, each independently represent a hydrocarbon group, optionally substituted, containing up to 20 carbon atoms, or the pairs $R_1$, $R_2$ and/or $R_3$, $R_4$, together with the nitrogen atom to which they are attached, form a heterocycle which can also contain one or more oxygen or sulfur heteroatoms;

$A_1$ and $A_2$ each independently, represent a linear or branched alkylene group, or an aryl group, optionally substituted, containing up to 20 carbon atoms;

X represents —$SO_2$— or —CO—;

$R_5$ and $R_6$ represent hydrogen or lower alkyl when X represents —$SO_2$—;

and $R_5$ and $R_6$, together, represent

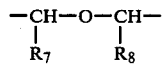

when X represents —CO—;

$R_7$ and $R_8$ represent hydrogen or lower alkyl;

$A_3$ represents alkylene or cycloalkylene, substituted or not, and saturated or not, containing from 2 to 20 carbon atoms and optionally being interrupted by a heteroatom or group of heteroatoms such as —O—, —S—, —SO—, —$SO_2$—, —S—S— or

or by one or more arylene or cycloalkylene groups, with $R_9$ being hydrogen, alkyl having 1–12 carbon atoms, cycloalkyl or aryl, optionally substituted, or $A_3$ represents polyoxyalkylene or —$B_1$—D—$B_2$—, wherein $B_1$ and $B_2$ represent alkylene having from 1 to 12 carbon atoms, or arylene, optionally substituted, and D represents a group having the following formula:

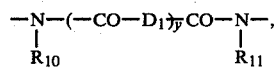

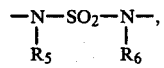

—CONH—, —CO—O—, —O—CONH—,
—CO—$D_2$—CO—, or
—O—CO—$D_3$—CO—O—, wherein $D_1$ represents alkylene, optionally interrupted by an —S—S— group, alkenylene, arylene, diaminoalkylene, diaminoarylene, dioxyalkylene, polyoxyalkylene or dioxyarylene, or $D_1$ represents a direct covalent bond, y is a number equal to 0 or 1, $R_{10}$ and $R_{11}$ represent hydrogen or lower alkyl, or when y=0, $R_{10}$ and $R_{11}$, together, also represent

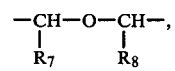

$D_2$ represents diaminoalkylene, dioxyalkylene, polyoxyalkylene or dithioalkylene, $D_3$ represents alkylene or arylene, substituted or not, diaminoalkylene, diaminocycloalkylene or diaminoarylene, or $A_3$, together with the two nitrogen atoms to which it is attached and with the pairs $R_1$, $R_3$ and/or $R_2$, $R_4$, represents a cyclic or polycyclic group having from 4 to 6 carbon atoms;

and $Z^\ominus$ represents an anion.

In the following description those polymers based on recurring units of Formula I, above, are designated by the expression "Formula I polymers".

The terminal groups of the Formula I polymers can vary, particularly with regard to the proportions of the reagents used in preparing them. For example, they can be of the

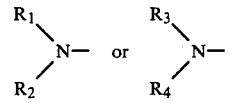

type or of the Z—$A_3$—, Z—$A_1$— or Z—$A_2$— type.

In Formula I, when $A_3$ represents alkylene or cycloalkylene, substituted or not, and optionally interrupted by one or more heteroatoms or arylene groups, $A_3$ represents, especially, groups having the formula:

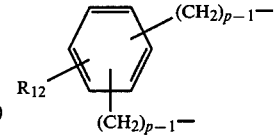

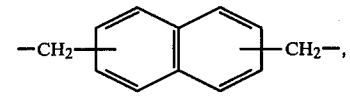

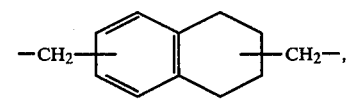

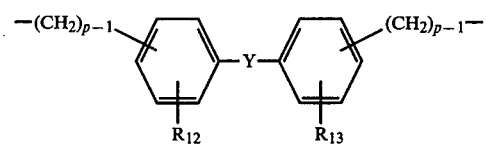

-continued

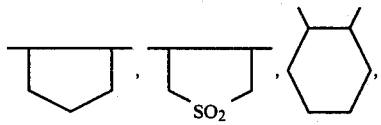

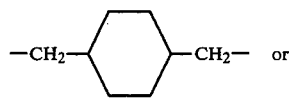

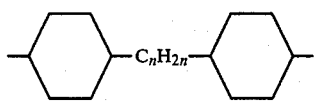

wherein $R_{12}$ and $R_{13}$ represent hydrogen, lower alkyl, lower hydroxyalkyl, halogen, carboxy, alkoxycarbonyl or phenyl, Y represents a direct covalent bond, or —O—, —CO—, —CHOH— or —SO$_2$— or alkylene, n is a number ranging from 1 to 6, p is a number ranging from 1 to 3;

when $A_3$, together with the two nitrogen atoms to which it is attached and with the pairs $R_1$, $R_3$ and/or $R_2$, $R_4$, represents a cyclic or polycyclic group, $A_3$ represents

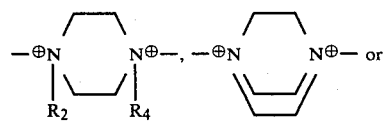

$R_2$ and $R_4$ being defined above;

when $Z^\ominus$ represents an anion derived from a mineral acid or derived from an organic acid with a low molecular mass, $Z^\ominus$ represents, in particular, a halide, nitrate, sulfate, acetate or paratoluene sulfonate anion; the substituents $R_1$, $R_2$, $R_3$ and $R_4$ represent, in particular, aryl, aliphatic (particularly alkyl or alkenyl), substituted or not, alicyclic (particularly cycloalkyl), or arylaliphatic containing a maximum of 20 carbon atoms; for example, $R_1$, $R_2$, $R_3$ and $R_4$ represent an alkyl or hydroxyalkyl having from 1 to 8 carbon atoms, cycloalkyl-alkyl having fewer than 20 carbon atoms and preferably having not more than 16 carbon atoms, cycloalkyl having 5 or 6 chains or aralkyl such as phenyl-alkyl wherein the alkyl moiety preferably has from 1 to 3 carbon atoms; when the pairs $R_1$ and $R_2$, or $R_3$ and $R_4$, attached to the same nitrogen atom represent, with it, a ring, they represent, in particular, polymethylene having from 2 to 6 carbon atoms and the ring can also include a heteroatom of oxygen or sulfur; $A_1$ and $A_2$ represent, in particular, linear or branched alkylene having from 1 to 12 carbon atoms in the chain, and optionally including one or more, and particularly from 1 to 4, branched alkyl substituents, with the said branched substituents having from 1 to 10, and particularly from 1 to 4, carbon atoms; $D_2$ represents, in particular, alkylene, defined as above for $A_1$ or $A_2$, the said alkylene group optionally being interrupted by an —S—S— group, or the said alkylene group optionally including an —NH— group or an —O— group at each end; or $D_1$ represents arylene having from 6 to 20 carbon atoms, such as

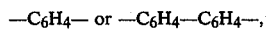

the said arylene group optionally being substituted by one or more alkyl groups having, particularly, from 1 to 3 carbon atoms and especially methyl or ethyl, and the said arylene group optionally including an —NH— or —O— group at each end;

$D_2$ represents —NH—alkylene—NH— or —O—alkylene—O— or —S—alkylene—S—, wherein the alkylene moiety is defined as above for $A_1$;

$D_3$ is alkylene, defined as for $A_1$, or arylene having from 6 to 20 carbon atoms, defined and optionally being substituted as for $D_1$, or cycloalkylene having from 5 to 20 carbon atoms, with the said group optionally including an —NH— group at each end.

It should be noted that the invention also relates to Formula I polymers wherein the —A$_1$—N(R$_5$)—X—N(R$_6$)—A$_2$— and/or A$_3$ groups having several different values in a single polymer chain.

The invention is not limited to Formula I polymers having a particular molecular weight range.

In general, the polymers of the present invention have an average molecular weight ranging from approximately 1,000 to 50,000.

The present invention also relates to a process for preparing the Formula I polymers.

This process consists in polycondensing at least one amine having the formula:

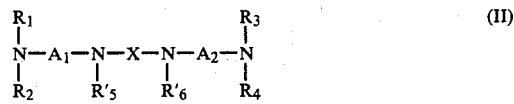

wherein $R'_5$ and $R'_6$ are defined as $R_5$ and $R_6$ above, with $R'_5$ and $R'_6$ also representing hydrogen when X represents —CO—, or an amine of the formula

with one or more dihalides having the formula:

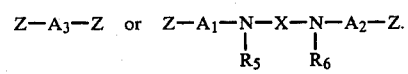

In the situation where $R'_5=R'_6$ and X=—CO—, the polymer which is obtained is reacted with an aldehyde having the formula $R_7$—CHO or $R_8$—CHO, wherein $R_7$ and $R_8$ are defined as above, at the rate of 2 moles of aldehyde per —NHCONH— group present in the said polymer, in the presence of an acid catalyst such as hydrochloric acid, to obtain the corresponding Formula I polymer, with X=CO and $R_5$ and $R_6$ representing, together, —CH(R$_7$)—O—CH(R$_7$)— or —CH(R$_8$)—O—CH(R$_8$).

In addition to the units of Formula I, the polymers of the present invention can also contain units of Formula I':

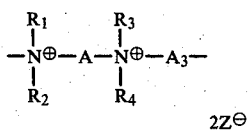

$$2Z^{\ominus}$$

wherein:

$R_1$, $R_2$, $R_3$, $R_4$, $A_3$ and Z are defined as above and A is alkylene, alkenylene or hydroxyalkylene containing from 3 to 20 carbon atoms, or polyoxyalkylene.

Such polymers can be obtained, in particular, by admixing with the amines of formula (II) and/or (III) at least one amine having the formula

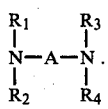

In general, the polymers of the present invention contain less than 90% by weight of Formula I' units.

The polycondensation reaction is carried out in a solvent or a mixture of solvents which favor quaternization reactions, such as water, dimethyl formamide, methyl cyanide, lower alcohols, particularly, lower alkanols such as methanol, etc.

The polycondensation reaction can be carried out under pressure, if necessary.

The reaction temperature can vary between 10° and 150° C., and preferably between 20° and 100° C.

The reaction time depends upon the nature of the solvent, the initial reactants and the degree of polymerization desired.

In general, the initial reactants are reacted in equimolecular quantities, although it is possible to use either the diamine or dihalide in slight excess, said excess being less than 20 mole percent.

The resulting polycondensate is isolated at the conclusion of the reaction, if desired, either by filtration or by concentrating the reaction mixture.

It is possible to control the average length of the chains by adding, at the beginning or during the course of the reaction, a slight quantity (from 1 to 15 mole percent, with respect to one of the reagents) of a monofunctional reagent such as a tertiary amine or a monohalide. In this instance, at least a portion of the terminal groups of the resulting Formula I polymer is made up of either the tertiary amine group which is used or of the hydrocarbon group of the monohalide.

To prepare the amines of Formula II, for which X represents —CO— and $R_5$ and $R_6$, together, represent a —CH($R_7$)—O—CH($R_8$)— group, an amine or a mixture of amines having the formula:

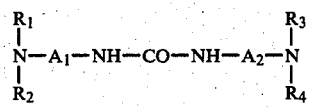

is reacted with one or more aldehydes having the formula, $R_7CHO$ or $R_8CHO$, in an acid environment, to form the salt of the desired amine, and the said resulting salt is transformed into a free amine by the action of a base.

Two moles of aldehyde per mole of initial amine reacted are employed.

To prepare the Formula II initial amine reactants wherein X=—SO$_2$—, an amine, or a mixture of amines, having the formula:

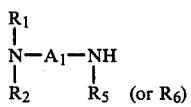

is reacted with sulfuryl chloride in an amount of two moles of amine per mole of sulfuryl chloride. The salt of the desired amine is obtained which is then transformed into a free amine by the action of a base.

The amines having Formula II:

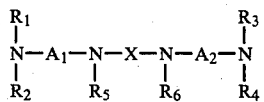

and their addition salts are also an object of the present invention.

In general, the polymers of the present invention are soluble in at least one of the three solvents consisting of water, ethyl alcohol or a mixture of water and ethyl alcohol.

On evaporation of their solution, it is possible to obtain films which, in particular, have a good affinity for hair.

The polymers of the present invention can be used in cosmetic compositions for the treatment of the hair and the skin. In particular, they improve the quality of the hair, facilitate treatments applied to the hair, facilitate combing and effectively contribute to eliminating deficiencies of the hair sensitized by treatments having a harmful effect.

The polymers of the present invention can also be used as agents to assist in the treatment of natural or synthetic textile fibers, such as antibacterial agents, dispersing agents or emulsifying or flocculating agents. For example, the polymers of the present invention can be used as preserving agents in adhesives or as additives in products for treating leather or cellulose derivatives, in particular, paper.

The following non-limiting examples illustrate the present invention.

EXAMPLES OF THE PREPARATION OF FORMULA II INITIAL REACTANT AMINES

As was described earlier, these diamines can be prepared in accordance with the following scheme, which is provided solely as an example:

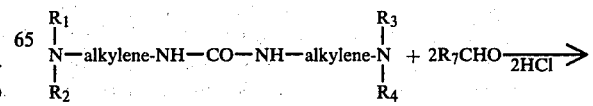

-continued

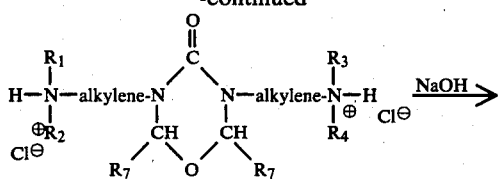

For example, the following operation can be employed.

PREPARATION NO. 1

A mixture containing 1.080 g of formaldehyde in a 30% aqueous solution and 674 cm³ of concentrated hydrochloric acid is heated to reflux. Then 621 g of 1,3-bis-(3-dimethylamino-propyl) urea are added drop by drop. The resulting mixture is heated to reflux, with agitation, for 25 minutes. The reaction mixture is permitted to cool and is then neutralized by adding 850 cm³ of concentrated soda.

The reaction mixture is then extracted with 400 cm³ of dichloromethane in four stages. The solvent is then evaporated under reduced pressure. 620 g of 3,5-bis-(3-dimethylamino propyl)-4-oxo-1,3,5-tetrahydrooxadiazine, having a purity greater than 95%, are obtained.

Boiling point: 165°–167° C. under 0.5 mm of Hg.

To prepare the Formula II initial reactant amine, the following operation is carried out:

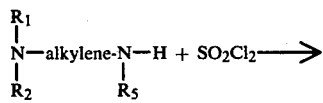

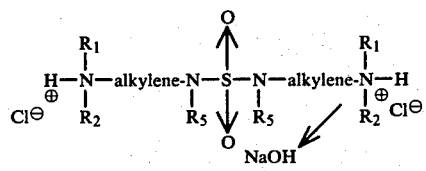

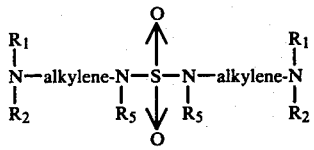

PREPARATION NO. 2

130 g of 1-amino-2,2-dimethyl-3-dimethylaminopropane are dissolved in 200 cm³ of dichloromethane. There is added, drop by drop, while agitating and maintaining the temperature at 45° C., a solution of 67.5 g of sulfonyl chloride in 100 cm³ of dichloromethane. The resulting mixture is agitated for 1 hour. The solvent is then evaporated under reduced pressure. The oily residue is dissolved in 200 cm³ of water and neutralized by the addition of 22 g of soda in 100 cm³ of water. The reaction mixture is filtered, washed in water and dried under reduced pressure.

After recrystallization in 60% ethyl alcohol, there are obtained 81 g of 1,3-bis-(2,2-dimethyl-3-dimethylaminopropyl) sulfamide in the form of a white crystalline powder melting at 103° C.

EXAMPLES OF THE PREPARATION OF FORMULA I POLYMERS

Example 1

Formula I polymer wherein
$A_1 = A_2 = -(CH_2)_3-$,
$R_1 = R_2 = R_3 = R_4 = CH_3$,
$X = -CO-$,
$R_5$ and $R_6$, together, represent $-CH_2-O-CH_2-$,
$A_3 = -(CH_2)_6-$ and $Z^{\ominus} = Cl^{\ominus}$ There are heated to reflux, for 3 hours while agitating,
40.88 g (0.15 mole) of 3,5-bis(3-dimethylamino propyl)-4-oxo-1,3,5-tetrahydrooxadiazine,
23.25 g (0.15 mole) of 1,6-dichloro hexane, and
50 g of water.

The reaction mixture is permitted to cool and the final concentration of the solution is adjusted to 50% (weight/weight).

Ionic halogen content: 100% of theoretical content.

Examples 2 and 3

Formula I polymers have been obtained wherein $R_1$, $R_2$, $R_3$, $R_4$, $R_5$, $R_6$, $A_1$, $A_2$, X and Z are defined as in Example 1 in a similar manner, and for which:
$A_3$ represents $-CH_2-CHOH-CH_2-$ (Example 2), and
$A_3$ represents $-CH_2-CH=CH-CH_2-$ (Example 3).
Chloride content:
Example 2: 96% of theoretical content,
Example 3: 95% of theoretical content.

Example 4

Formula I polymer wherein
$A_1$, $A_2$, $R_5$, $R_6$, X and Z are defined as in Example 1,
$R_1 = R_2 = R_3 = R_4 = C_2H_5$, and $A_3 = -(CH_2)_6-$.

There are heated to reflux, for 3 hours while agitating,
55 g (0.192 mole) of 1,3-bis(3-diethylamino propyl) urea,
29.76 g (0.192 mole) of 1,6-dichloro-hexane, and
50 g of water.

The reaction mixture is permitted to cool and there are then added 38.4 g (0.384 mole) of formaldehyde in 30% aqueous solution and 4 cm³ of concentrated hydrochloric acid. The mixture is heated at 95° C. for one hour, after which it is permitted to cool. The final concentration of the solution is adjusted to 50% (weight/weight).

Ionic chlorine content: 100% of theoretical content.

Examples 5–7

The following Formula I polymers have been obtained for which $R_1$, $R_2$, $R_3$, $R_4$, $R_5$, $R_6$, $A_1$, $A_2$, X and Z are defined as in Example 4, in a similar manner, and wherein
$A_3$ represents $-CH_2-CHOH-CH_2-$ (Example 5: chloride 90% of theoretical content);
$A_3$ represents $-CH_2-CH=CH-CH_2-$ (Example 6: chloride 97% of theoretical content); and $A_3$ represents —$(CH_2)_2$—O—$(CH_2)_2$— (Example 7: chloride 99% of theoretical content).

Example 8

Formula I polymer wherein
$R_1$, $R_2$, $R_3$, $R_4$, $R_5$, $R_6$, $A_1$, $A_2$, X and Z are defined as in Example 1, and
$A_3$ represents p-xylylenyl.

There are heated to reflux, for 3 hours,
32.64 g (0.12 mole) of 3,5-bis(3-dimethylaminopropyl)-4-oxo-1,3,5-tetrahydrooxadiazine,
31.7 g (0.12 mole) of 1,4-bis(bromomethyl)benzene, and
150 g of methanol.

At the conclusion of the reaction, the reaction mixture is permitted to cool and the solvent is distilled off under reduced pressure. After dissolving in water, the final product is obtained in the form of a 50% aqueous solution (weight/weight).

Chloride content: 100% of theoretical content.

Example 9

Formula I polymer wherein
$R_1$, $R_2$, $R_3$, $R_4$, $A_1$, $A_2$ and Z are defined as in Example 1,
X=—$SO_2$— and
$A_3$=—$(CH_2)_2$—O—$(CH_2)_2$—.

There are heated to reflux, for 3 hours, while agitating,
26.6 g (0.1 mole) of 1,3-bis(3-dimethylaminopropyl) sulfonamide, and 14.3 g of dichlorodiethylether, in 30 g of water.

The reaction mixture is permitted to cool and the final concentration of the solution is adjusted to 50% (weight/weight).

Ionic halogen content: 100% of theoretical content.

Example 10

Formula I polymer wherein
$R_1=R_2=R_3=R_4=CH_3$, $R_5=R_6=H$,
$A_1=A_2=$—$CH_2$—$C(CH_3)_2$—$CH_2$—, X=—$SO_2$—,
$A_3=$—$(CH_2CH_2O$—$)_2$— $CH_2CH_2$— and $Z^\ominus=Cl^\ominus$ There are heated to reflux 32.2 g (0.1 mole) of 1,3-bis-(2,2-dimethyl-3-dimethyl-amino propyl) sulfamide, 18.7 g (0.1 mole) of 1,2-bis(2-chloro-ethoxy) ethane and 50 g of water for 200 hours, while agitating. The reaction mixture is permitted to cool and the final concentration of the solution is adjusted to 50% (weight/weight).

Ionic halogen content (percentage of theoretical content): 80%.

Examples 11–14

Using a process similar to that described in Example 10, mixtures of dihalides and diamines (equimolecular proportions of dihalides and diamines) are reacted. The following dihalides and diamines have been used:

$A_c$
$CH_3$  $CH_3$            $CH_3$  $CH_3$
|      |                |      |
N—$CH_2$—C—$CH_2$—NH—$SO_2$—NH—$CH_2$—C—$CH_2$—N
|      |                |      |
$CH_3$  $CH_3$            $CH_3$  $CH_3$ $A_d$
$CH_3$            $CH_3$
|                |
N—$CH_2$—CHOH—$CH_2$—N
|                |
$CH_3$            $CH_3$ $A_e$
           O
           ‖
$CH_3$     C          $CH_3$
|       /   \          |
N($CH_2$)$_3$—N       N—($CH_2$)$_3$—N
|         \           /        |
$CH_3$    $CH_2$  $CH_2$       $CH_3$
           \   /
            O $A_b$
$CH_3$            $CH_3$
|                |
N—($CH_2$)$_3$—N
|                |
$CH_3$            $CH_3$ $B_b$
Cl—($CH_2$)$_6$—Cl.

| Example No. | Quaternary polymers prepared by starting with (moles) | Ionic Halogen content (percentage of theoretical content) |
|---|---|---|
| 11 | $\frac{1}{2} A_c + \frac{1}{2} A_b + (1) B_b$ | 90% |
| 12 | $\frac{1}{4} A_c + \frac{3}{4} A_b + (1) B_b$ | 90% |
| 13 | $\frac{3}{4} A_e + \frac{1}{4} A_b + (1) B_b$ | 95% |
| 14 | $\frac{1}{2} A_e + \frac{1}{2} A_d + (1) B_b$ | 96% |

Example 15

Formula I polymer wherein:
$R_1=R_2=R_3=R_4=CH_3$,
$A_1=A_2=$—$(CH_2)_3$—,
X=—CO—,
$R_5$ and $R_6$, together, represent —$CH_2$—O—$CH_2$—,
$A_3=$—$CH_2$—$C_6H_4$—$C_6H_4$—$CH_2$— and
$Z^\ominus=Cl^\ominus$.

There are heated to reflux for 12 hours, while agitating,
13.6 g (0.05 mole) of 3,5-bis(3-dimethylamino propyl)-4-oxo-1,3,5-tetrahydro oxadiazine,
12.55 g (0.05 mole) of 4,4'-bis(chloromethyl) biphenyl, and 100 cm³ of methanol.

At the conclusion of the reaction, the reaction mixture is permitted to cool. The solvent is distilled off under reduced pressure. The residue is washed in dichloromethane and dried.

The resulting polymer has an ionic chlorine content of 82% of the theoretical value.

The product described in the following example was obtained in a similar manner.

Example 16

Formula I polymer wherein
$R_1=R_2=R_3=R_4=CH_3$,
$A_1=A_2=CH_2$—$C(CH_3)_2$—$CH_2$,
X=$SO_2$,
$R_5=R_6=H$,
$A_3=$—$CH_2$—$C_6H_4$—$C_6H_4$—$CH_2$— and
$Z^\ominus=Cl^\ominus$.

Ionic halogen content: 87% of theoretical value.

Example 17

Formula I polymer wherein
$R_1=R_2=R_3=R_4=CH_3$, $A_1=A_2=-(CH_2)_3-$, $X=-CO-$,
$R_5$ and $R_6$, together, represent $-CH_2-O-CH_2-$,
$A_3=-CH_2-CO-NH-C(CH_3)_2-(CH_2)_4-C(CH_3)_2-NH-CO-CH_2$ and $Z^\ominus=Cl^\ominus$ There are heated to reflux, in 50 cm³ of water, a mixture of:
0.1 mole of Formula II amine wherein $R_1$, $R_2$, $R_3$, $R_4$, $R_5$, $R_6$, $A_1$, $A_2$ and $X$ are defined as above, and 0.1 mole of $ClCH_2CONH-C(CH_3)_2-(CH_2)_4-C(CH_3)_2-NHCOCH_2Cl$.

At the conclusion of the reaction, the water is removed under reduced pressure and the residue is washed in acetone and dried. The resulting polymer has a Cl content equal to 93.4% of the theoretical value.

The polymer of the following example is obtained in a similar manner.

Example 18

Formula I polymer wherein
$R_1=R_2=R_3=R_4=CH_3$, $A_1=A_2=-(CH_2)_3-$,
$X=-CO-$,
$R_5$ and $R_6$, together, represent $-CH_2-O-CH_2$,
$A_3=-(CH_2)_2-CO-NH-C(CH_3)_2-(CH_2)_6-C(CH_3)_2-NH-CO-(CH_2)_2-$ and
$Z^\ominus=Cl^\ominus$.
Cl content: 98.5% of theoretical value.

Example 19

Operating as in Examples 11–14 and starting with a mixture of diamines and an equimolecular mixture of dihalides, the following copolymer was prepared wherein
$R_1=R_2=R_3=R_4=CH_3$ and $Z^\ominus=Cl^\ominus$ and wherein
for 20% of the units, $A_3$ is $(CH_2)_3$;
for 20% of the units, $A_3$ is $-(-CH_2CH_2-O-)_2CH_2CH_2-$;
for 20% of the units, $A_3$ is $-CH_2-CO-NH-C(CH_3)_2-(CH_2)_4-C(CH_3)_2-NH-CO-CH_2-$;

for 20% of the units, $A_3$ is $-CH_2-C_6H_4-C_6H_4-CH_2$; and
for 20% of the units, $A_3$ represents $-(CH_2)_2-O-(CH_2)_2-$,
while
for 50% of the units, $A_1=A_2=(CH_2)_3$;
$X=-CO-$ and
$R_5+R_6=-CH_2-O-CH_2$;
and for 50% of the units
$A_1=A_2=-CH_2-C(CH_3)_2-CH_2-$,
$X=-SO_2-$ and $R_5=R_6=H$.
Cl⁻ content: 92% of theoretical content.

We claim:
1. A polymer having units of the formula

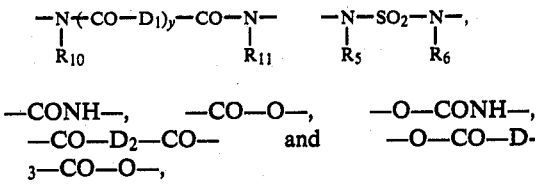

wherein
$R_1$, $R_2$, $R_3$ and $R_4$, each independently represent a hydrocarbon group containing up to 20 carbon atoms, or at least one pair selected from the group consisting of $R_1$, $R_2$ and $R_3$, $R_4$, together with the nitrogen atom to which it is attached, forms a heterocycle selected from the group consisting of a heterocycle wherein the heteroatom is nitrogen and a heterocycle containing nitrogen as a first heteroatom and a second heteroatom selected from the group consisting of oxygen and sulfur;
$A_1$ and $A_2$ each independently represents a linear or branched alkylene, or aryl, containing up to 20 carbon atoms;
$X$ represents $-SO_2-$ or $-CO-$;
$R_5$ and $R_6$ represent hydrogen or lower alkyl when $X$ represents $-SO_2-$;
or $R_5$ and $R_6$, together, represent $$-\underset{R_7}{CH}-O-\underset{R_8}{CH}-$$

when $X$ represents $-CO-$;
$R_7$ and $R_8$ represent hydrogen or lower alkyl;
$A_3$ represents alkylene, cycloalklene, alkenylene or cycloalkenylene, containing 2 to 20 carbon atoms, or at least one or said alkylene, cycloalkylene, alkenylene and cycloalkylene, interrupted by at least one heteroatom or by at least one of an arylene or cycloalkylene group, or
$A_3$ represents polyoxyalkylene or $-B_1-D-B_2-$ wherein $B_1$ and $B_2$ represent alkylene having from 1 to 12 carbon atoms, or arylene, and $D$ represents a member selected from the group consisting of $$-\underset{R_{10}}{N}(-CO-D_1)_y-CO-\underset{R_{11}}{N}- \quad -\underset{R_5}{N}-SO_2-\underset{R_6}{N}-,$$

$-CONH-$, $-CO-O-$, $-O-CONH-$,
$-CO-D_2-CO-$ and $-O-CO-D_3-CO-O-$,
wherein
$D_1$ represents alkylene, alkylene interrupted by a $-S-S-$ group, alkenylene, arylene, diaminoalkylene, diaminoarylene, dioxyalkylene, polyoxyalkylene or dioxyarylene, or
$D_1$ represents a direct covalent bond,
$y$ is a number equal to 0 or 1,
$R_{10}$ and $R_{11}$ represent hydrogen or lower alkyl, or when $y$ is 0, $R_{10}$ and $R_{11}$, together, represent $$-\underset{R_7}{CH}-O-\underset{R_8}{CH}-,$$

$D_2$ represents diaminoalkylene, dioxyalkylene, polyoxyalkylene or dithioalkylene,
$D_3$ represents alkylene, arylene, diaminoalkylene, diaminocycloalkylene or diaminoarylene, or
$A_3$, together with the two nitrogens to which it is attached and with at least one of the pairs $R_1$, $R_3$ and $R_2$, $R_4$, represents a cyclic or polycyclic group having from 4 to 6 carbon atoms; and
$Z^\ominus$ represents an anion.
2. The polymer of claim 1 wherein, when $A_3$ represents alkylene or cycloalkylene, $A_3$ represents a member selected from the group consisting of

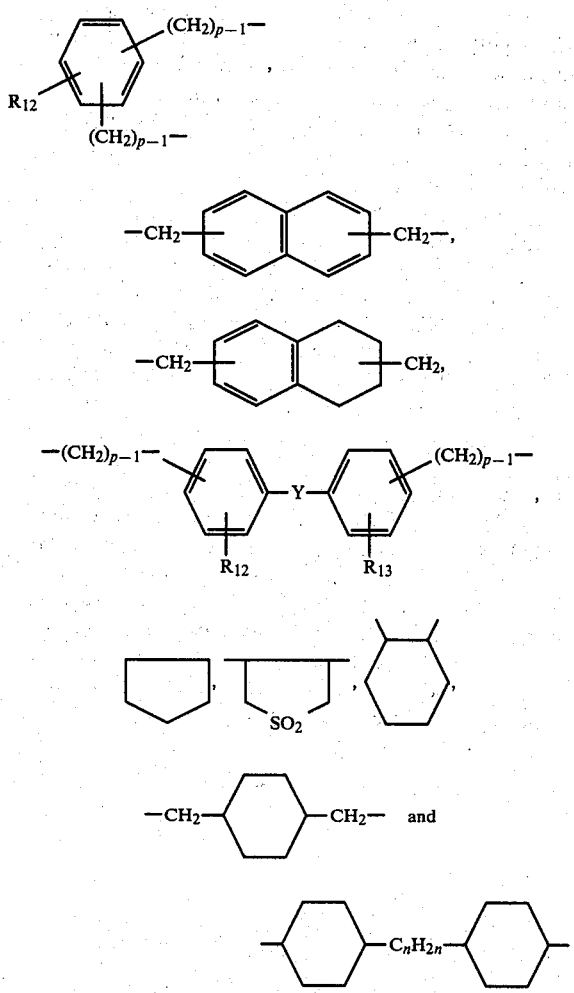

wherein
  $R_{12}$ and $R_{13}$ represent hydrogen, lower alkyl, lower hydroxyalkyl, halogen, carboxy, alkoxycarbonyl or phenyl,
  Y represents a direct covalent bond, or Y represents —O—, —CO—, —CHOH—, —SO$_2$— or alkylene,
  n is a number ranging from 1 to 6; and
  p is a number ranging from 1 to 3.

3. The polymer of claim 1 wherein, when $A_3$ represents a cyclic or polycyclic group, $A_3$ represents a member selected from the group consisting of

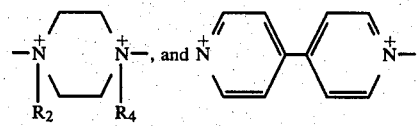

where $R_2$ and $R_4$ are defined in claim 1.

4. The polymer of claim 1 wherein $Z^-$ represents an anion derived from a mineral acid or low molecular weight organic acid.

5. The polymer of claim 4 wherein $Z^-$ represents a halide, nitrate, sulfate, acetate or paratoluene sulfonate anion.

6. The polymer of claim 1 wherein $R_1$, $R_2$, $R_3$ and $R_4$ each independently, represent an aryl, aliphatic, alicyclic or arylaliphatic group containing a maximum of 20 carbon atoms.

7. The polymer of claim 6 wherein $R_1$, $R_2$, $R_3$ and $R_4$ each independently represent alkyl or hydroxyalkyl containing 1-8 carbon atoms, cycloalkyl-alkyl having less than 20 carbon atoms, cycloalkyl having 5 or 6 carbon atoms or aralkyl wherein the alkyl group contains 1-3 carbon atoms.

8. The polymer of claim 1 wherein, when at least one of the pairs $R_1$, $R_2$ and $R_3$, $R_4$ together with the nitrogen atom to which it is attached forms a ring, said pair represents a polymethylene group having 2 to 6 carbon atoms.

9. The polymer of claim 1 wherein $A_1$ and $A_2$ each independently represents linear or branched alkylene having 1-12 carbon atoms or linear or branched alkylene having 1-12 carbon atoms substituted by 1-4 branched alkyl substituents wherein said alkyl contains 1-10 carbon atoms.

10. The polymer of claim 1 wherein $A_3$ represents —$B_1$—D—$B_2$— wherein D represents —N($R_{10}$)—(CO—$D_1$)$_y$ CO—N($R_{11}$)— wherein $D_1$ represents linear or branched alkylene having 1-12 carbon atoms, linear or branched alkylene having 1-12 carbon atoms and having at least one branched alkyl substituent having 1-10 carbon atoms, linear or branched alkylene having 1-12 carbon atoms and being interrupted by a —S—S— group or linear or branched alkylene having 1-12 carbon atoms and including an —NH— or —O— group at each end thereof, or $D_1$ represents arylene having 6-20 carbon atoms, arylene having 6-20 carbon atoms and being substituted by at least one allyl group having 1-3 carbon atoms or arylene having 6-20 carbon atoms and including an —NH— or —O— group at each end.

11. The polymer of claim 1 wherein $D_2$ represents —NH—alkylene—NH—, —O—alkylene—O— or —S—alkylene-S- wherein the alkylene moiety has 1-12 carbon atoms.

12. The polymer of claim 1 wherein $D_3$ is linear or branched alkylene having 1-12 carbon atoms, linear or branched alkylene having 1-12 carbon atoms and having at least one branched alkyl substituent having 1-10 carbon atoms or linear or branched alkylene having 1-12 carbon atoms and having an —NH— group at each end thereof or $D_3$ is arylene having 6-20 carbon atoms, arylene having 6-20 carbon atoms and being substituted by at least one alkyl group, or arylene having 6-20 carbon atoms and having an —NH— group at each end thereof.

13. The polymer of claim 1 wherein $D_3$ represents cycloalkylene or —NH—cycloalkylene—NH— wherein said cycloalkylene has from 5 to 20 carbon atoms.

14. The polymer of claim 8 wherein said ring contains a heteroatom selected from the group consisting of oxygen and sulfur.

15. A polymer having units of the formula

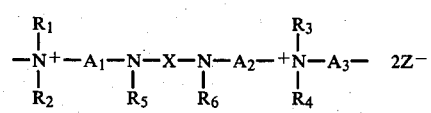

wherein
  $R_1$, $R_2$, $R_3$ and $R_4$ each independently represent alkyl having up to 20 carbon atoms;

$A_1$ and $A_2$ each independently represent alkylene containing up to 20 carbon atoms;

X represents —CO—;

$R_5$ and $R_6$, together, represent

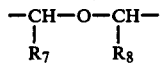

wherein $R_7$ and $R_8$ represent hydrogen or lower alkyl, $A_3$ represents alkylene containing 2 to 20 carbon atoms, and $Z^-$ represents an anion.

16. The polymer of claim 15, wherein $A_1$ equals $A_2$ equals —$(CH_2)_3$—; $R_1$ equals $R_2$ equals $R_3$ equals $R_4$ equals $CH_3$; $R_5$ and $R_6$, together, represent —$CH_2$—O—$CH_2$—; $A_3$ equals —$(CH_2)_6$— and $Z^-$ equals $Cl^-$.

17. A process for preparing the polymer of claim 1 comprising polycondensing at least one amine selected from the group consisting of an amine of the formula $R_1R_2N$—$A_1$—$N(R'_5)$—X—$N(R'_6)$—$A_2$—$N$—$R_3R_4$ (II) wherein $R'_5$ and $R'_6$ have the meanings given for $R_5$ and $R_6$ in claim 39 or $R'_5$ and $R'_6$ also represent hydrogen when X represents —CO— and an amine of the formula $R_1R_2N$—$A_3$—$NR_3R_4$ (III) with at least one dihalide selected from the group consisting of Z—$A_3$—Z and Z—$A_1$—$N(R_5)$—X—$N(R_6)$—$A_2$—Z, wherein $R_1$, $R_2$, $A_1$, X, $A_2$, $R_3$, $R_4$, $R_5$, $R_6$ and $A_3$ have the meanings given in claim 1, with the proviso that when $R'_5$ equals $R'_6$ equals H and X equals —CO—, the resulting intermediate polymer is reacted in the presence of an acid catalyst with an aldehyde having the formula $R_7$—CHO wherein said aldehyde is present in an amount of two moles thereof per —NH—CO—NH— group present in said intermediate polymer so as to produce the polymer of claim 1.

18. The process of claim 17 wherein said amine of formula II for which X represents —CO— and $R_5$ and $R_6$, together, represent —$CH(R_7)$—O—$CH(R_8)$— is prepared by reacting at least one amine of the formula $R_1R_2N$—$A_1$—NHCONH—$A_2$—$NR_3R_4$ with at least one aldehyde selected from the group consisting of $R_7CHO$ and $R_8CHO$ in an acid environment so as to form the salt of the resulting amine and thereafter transforming said salt into the free amine by reaction with a base.

19. The process of claim 17 wherein said amine of formula II for which X represents —$SO_2$— is prepared by reacting at least one amine selected from the group consisting of $R_1R_2N$—$A_1$—$NHR_5$ and $R_1R_2N$—$A_1$—$NHR_6$ with sulfuryl chloride wherein said amine is present in an amount of two moles thereof per mole of sulfuryl chloride so as to form the salt of the resulting amine and thereafter transforming said salt into the free amine by reaction with a base.

* * * * *